US00PP08311P

United States Patent [19]

Vletter

[11] Patent Number: Plant 8,311

[45] Date of Patent: Jul. 20, 1993

[54] LILY PLANT NAMED CON AMORE

[75] Inventor: Floris Vletter, Rijnsburg, Netherlands

[73] Assignee: Gebr. Vletter & J.A. den Haan, Rijnsburg, Netherlands

[21] Appl. No.: 796,547

[22] Filed: Nov. 21, 1991

[51] Int. Cl.[5] ..... A01H 5/00

[52] U.S. Cl. ..... Plt./87.4

[58] Field of Search ..... Plt./87.4

*Primary Examiner*—James R. Feyrer

*Attorney, Agent, or Firm*—Foley & Lardner

[57] ABSTRACT

A new and distinct cultivar of lily plant named Con Amore, characterized by its unique lavender pink flower color with darker pink midveins and tepal edges, contrasting orange pollen and purple stigma, dark pink spots which are sometimes elongated to form lines 0.5 mm to 1.5 mm, medium to tall height, and high flower production based on bulb size.

1 Drawing Sheet

The present invention comprises a new and distinct cultivar of lily, botanically known as Lilium, known commercially as Lilium oriental hybrid, and hereinafter referred to by the cultivar name Con Amore. The parents were oriental varieties belonging to division VII(b) described in "Classification of Lily Cultivars into Divisions" published by Victoria Mathews, The Royal Botanic Gardens, Kew (1989).

The new cultivar is a product of a planned breeding program which had the objectives of creating new lily cultivars with attractive pink flower color, a good attitude or orientation of the flowers relative to the stem, and having a stem height and other features to adapt the cultivars to cut flower production.

The new cultivar was originated from a hybridization made by the inventor in a controlled breeding program in Rijnsburg, The Netherlands in 1983. Both the male and the female parent were unnamed seedlings.

The new cultivar was discovered and selected as one flowering plant within the progeny of the stated cross by the inventor in July 1983 in a controlled environment in Rijnsburg, The Netherlands.

The first act of asexual reproduction of the new cultivar was accomplished by the inventor when scales were taken from the initial selection in 1987 in a controlled environment in Rijnsburg, The Netherlands.

Horticultural examination of selected units has demonstrated that the combination of characteristics as herein disclosed for Con Amore are firmly fixed and are retained through successive generations of asexual reproduction.

The new cultivar has not been observed under all possible environmental conditions. The phenotype may vary somewhat with variations in environment such as temperature, light intensity, and day length, without, however, varying the genotype. The following observations, measurements and comparisons describe plants grown in Wageningen and Rijnsburg, The Netherlands under greenhouse conditions which approximate those generally used in commercial practice.

The following traits have been repeatedly observed and are determined to be basic characteristics of the new cultivar which in combination distinguish this lily as a new and distinct cultivar.

1. A very attractive lavender pink flower color;
2. Contrasting orange pollen and purple stigma;
3. Medium to tall growth habit;

4. A relatively large number of flowers are produced from regular bulb size;
5. Dark pink spots which are sometimes elongated to form lines;
6. Medium to tall height.

Of the many commercial cultivars known to the present inventor, the most similar in comparison to the new cultivar is Acapulco, disclosed in a pending application of the present inventor. In comparison to Acapulco, the new cultivar has a lighter pink flower, darker pollen and more flower production from the same size bulb. When flowering is forced under natural light, Con Amore produces an inflorescence approximately 15 days later than Stargazer, grown under the same conditions. Con Amore is fertile.

The accompanying photographic drawing shows typical flower characteristics of the new cultivar, with colors being as true as possible with illustrations of this type. The photograph comprises a top perspective showing open flowers and buds at various stages.

In the following description, color references are made to The Royal Horticultural Society (R.H.S.) Colour Chart. The color values were determined at Wageningen in 1989–1990 and at Rijnsburg in July 1991.

Origin: Seedling from Breeding Program.

Parentage:

*Seed parent.*—Unnamed seedling.

*Pollen parent.*—Unnamed seedling.

Classification:

Botanical.—Lilium.

Commercial.—Oriental hybrid.

THE PLANT

Form: A single stem carrying numerous pedicels alternately arranged.

Height: Medium to tall; 120 cm at time of opening of anthers of first flower.

Growth habit: Vigorous.

Stem: Circular in transverse section; internodal length uniform, 2 cm; light green with lighter spots 145B; no anthocyanin.

Foliage:

*Quantity.*—35–45 leaves depending on growing conditions.

*Size of leaf.*—Mature leaves are short to medium length, 16 cm; width is medium, 5.5 cm.

*Shape of leaves.*—Ovate.

*Texture.*—Smooth with weak glossiness on upper side.

*Color.*—Medium green 137A.

Bulbs:

*Size.*—Outlet 6–30 cm.

*Color.*—Yellow and purple.

Roots: Both stem and contractile present.

THE BUD

Form: Tapering (like a lancet).

Size: 11 cm.

Opening: Unfolds normally.

Color: 75C prior to opening.

Tepals: Folded, three visible.

THE FLOWER

Blooming habit: Raceme.

Size: Approximately 17 cm in total diameter, depending on growing conditions.

Borne: Upright.

Shape: Generally in form of hexagonal star; bowl-shaped; tips bend downwardly.

Tepalage:

*Number of tepals.*—Six.

*Arrangement.*—Three inner and three outer.

*Color.*—Upper surface: Pink 65C-D; darker along midvein and tepal edges. Lower surface: Slightly darker than 65D.

*Spotting or marking.*—Very intense pink spots, which are sometimes elongated to form lines approximately 1.5–0.5 mm in size.

Nectaries and papillae: Present.

Pedicel:

*Length.*—11 cm (the first flower).

*Color.*—Medium green.

*Form.*—Slightly curved.

Texture: Papillose.

Disease resistance: No disease problems noted to date.

Fragrance: Absent.

Lasting quality: Excellent.

REPRODUCTIVE ORGANS

Stamens, anthers:

*Arrangement.*—Anthers form a generally circular pattern.

*Length.*—Short, 7 cm.

*Number.*—Six.

*Filaments.*—Green.

Pollen color: Orange brown.

Anther color: Reddish brown.

Pistils: One with green style; total length of pistil 9 mm.

Stigma: Purple.

Ovaries: Triangular in shape; other characteristics typical of oriental lily varieties.

I claim:

1. A new and distinct cultivar of lily plant named Con Amore, as illustrated and described.

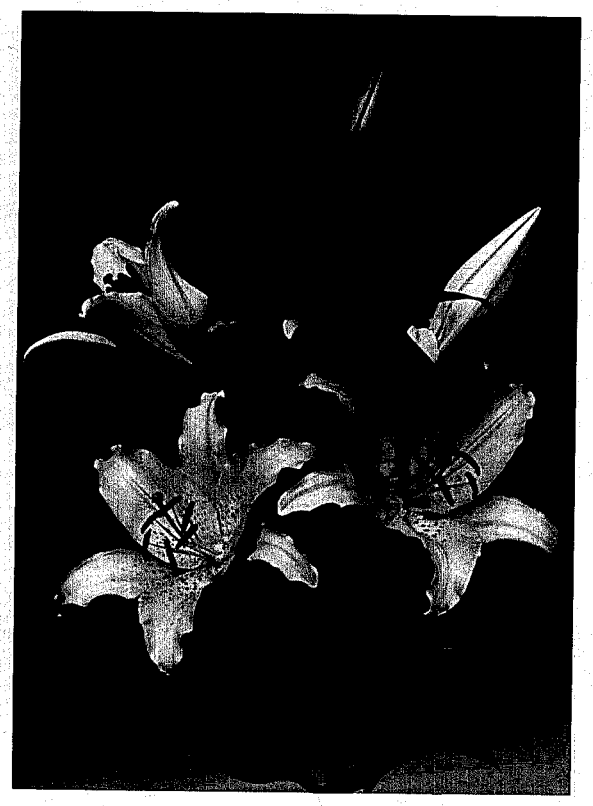

* * * * *